United States Patent [19]

Groshong et al.

[11] Patent Number: 4,898,579

[45] Date of Patent: Feb. 6, 1990

[54] INFUSION PUMP

[75] Inventors: Leroy E. Groshong, Portland; Judson C. Groshong, Beaverton, both of Oreg.; R. James Brawn, deceased, late of Portland, Oreg., by Stanley C. Fisher, administrator

[73] Assignee: Pump Controller Corporation, Portland, Oreg.

[21] Appl. No.: 201,951

[22] Filed: Jun. 3, 1988

Related U.S. Application Data

[62] Division of Ser. No. 67,700, Jun. 26, 1987, Pat. No. 4,838,860.

[51] Int. Cl.$^4$ .............................................. A61M 5/00
[52] U.S. Cl. ...................................... 604/67; 604/152; 128/DIG. 12
[58] Field of Search ................ 128/DIG. 1, DIG. 12, 128/DIG. 13; 604/31, 65, 67, 131, 151–155

[56] References Cited

U.S. PATENT DOCUMENTS

| | | |
|---|---|---|
| 3,447,479 | 6/1969 | Rosenberg . |
| 3,456,648 | 7/1969 | Lee et al. . |
| 3,701,345 | 10/1972 | Heilman et al. . |
| 3,731,679 | 5/1973 | Wilhelmson et al. . |
| 3,736,930 | 6/1973 | Georgi . |
| 3,737,251 | 6/1923 | Berman et al. . |
| 3,739,943 | 6/1973 | Wilhelmson et al. . |
| 3,841,799 | 10/1974 | Spinosa et al. . |
| 3,858,581 | 1/1975 | Kamen . |
| 3,901,231 | 8/1975 | Olson . |
| 3,985,133 | 10/1976 | Jenkins et al. . |
| 3,994,294 | 11/1976 | Knute . |
| 4,130,769 | 12/1979 | Karube ................................ 310/156 |
| 4,137,913 | 2/1979 | Georgi ......................... 128/DIG. 12 |
| 4,221,543 | 9/1980 | Cosentino et al. .......... 128/DIG. 12 |
| 4,261,360 | 4/1981 | Perez ...................................... 604/67 |
| 4,367,435 | 1/1983 | Bailey et al. . |
| 4,498,843 | 2/1985 | Schneider et al. ...................... 604/67 |
| 4,501,531 | 2/1985 | Bilstad et al. ......................... 604/67 |
| 4,604,034 | 8/1986 | Wheeldon et al. .................... 604/67 |
| 4,722,734 | 2/1988 | Kolln .................................... 604/67 |
| 4,731,057 | 3/1988 | Tanaka et al. ........................ 604/67 |

Primary Examiner—Stephen C. Pellegrino
Assistant Examiner—Ralph Lewis
Attorney, Agent, or Firm—Chernoff, Vilhauer, McClung & Stenzel

[57] ABSTRACT

An infusion pump for administering fluid from a fluid source to a patient comprises a base member having an electric motor for driving a fluid pump housed within a cassette detachably mountable on the base and connectable to the motor. The cassette houses a reciprocative piston and cylinder assembly which both pumps fluid to the patient while simultaneously drawing fluid from the fluid source so as to maintain a continuous flow rate of fluid to the patient. The cassette also houses deformably closable pairs of tubes connecting each of the pump's two fluid chambers to the cassette inlet and outlet respectively to provide the necessary valving to produce continuous flow in cooperation with the reciprocative piston and cylinder assembly. The fluid flow rate is adjustable controlled by a microcomputer which regulates the motor by repeatedly initiating electric motor driving pulses at a predetermined time rate, and terminating them in response to the advancement of the motor beyond one of a plurality of predetermined positions so as to maximize accuracy and reliability of flow rate while compatibly maximizing the power efficiency of the motor for portable applications requiring a battery power source.

10 Claims, 5 Drawing Sheets

FIG. 14

| HALLS | +V | GND |
|---|---|---|
| 011 | B | C |
| 111 | A | C |
| 110 | A | B |
| 100 | C | B |
| 000 | C | A |
| 001 | B | A |

COUNTER CLOCKWISE ↓    CLOCKWISE ↑

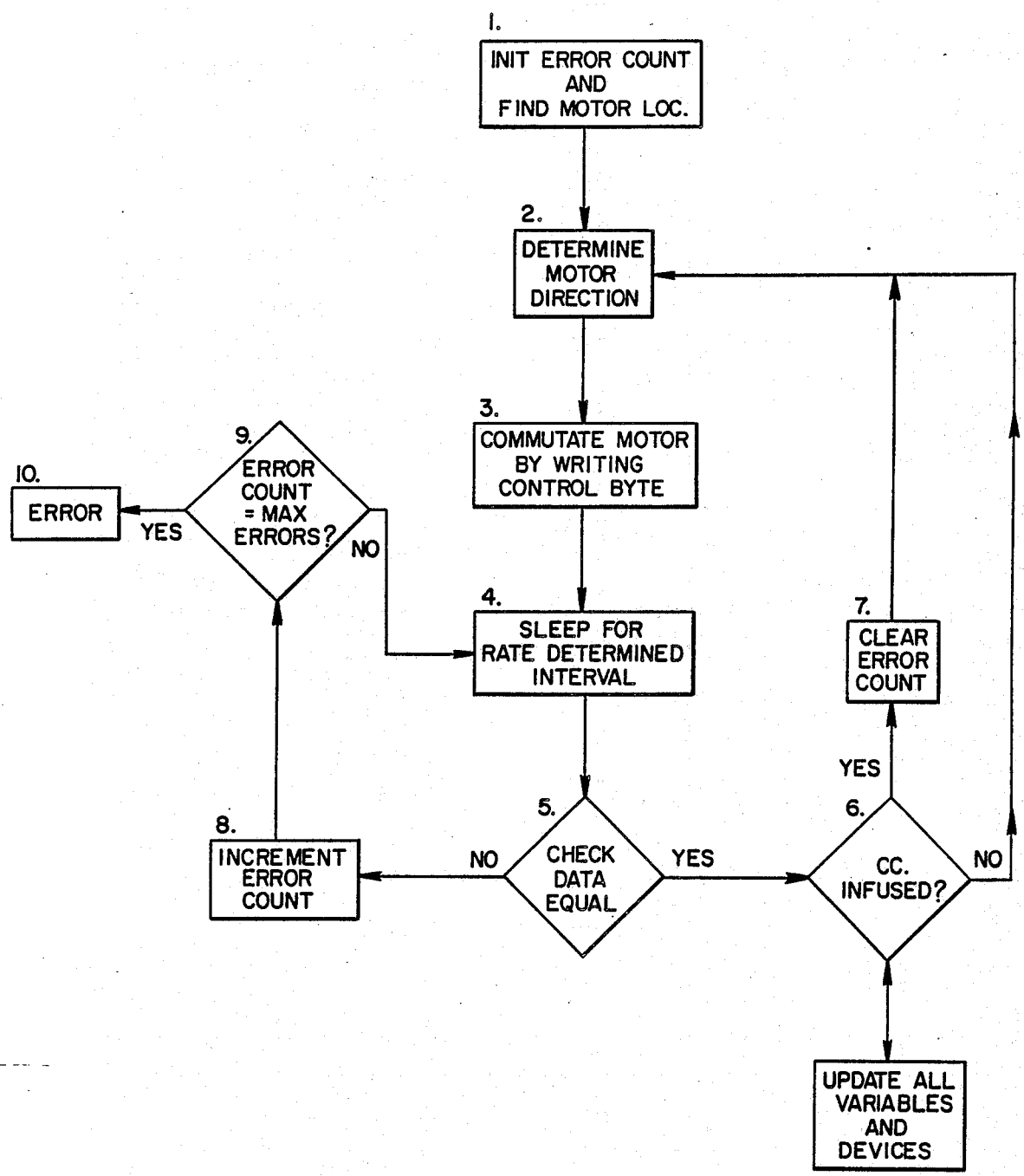

INFUSION PUMP

This application is a division of application Ser. No. 067,700, filed JUne 26, 1987, now U.;S. Pat. No. 4,838,860.

BACKGROUND OF THE INVENTION

This invention relates to infusion pumps for administering fluid from a fluid source to a patient. More particularly, the invention relates to a highly portable, compact, pump having readily disposable and replaceable cassette-type pump and valve components, and capable of administering fluid to a patient at a flow rate which is substantially continuous and precisely controlled.

Previous infusion pumps for supplying fluids to patients can be classified generally as syringe type and peristaltic type. Among the syringe type infusion pumps are those shown in the following U.S. Pat. Nos.: 3,447,479; 3,701,345; 3,731,679; 3,739,943; 3,858,581; 3,901,231; 3,985,133; and 4,367,435. These syringe pumps all share the common characteristic of employing an electric motor to drive the plunger of a syringe so as to expel fluid therefrom at a controlled flow rate for administration to a patient. All syringe pumps likewise share the common problem of being incapable of providing a substantially continuous flow rate to the patient because of the necessity to interrupt delivery of the fluid while the plunger is being retracted to refill the syringe after it has been emptied. The resultant intermittent interruption of fluid flow to the patient during such refilling introduces a troublesome variable into flow rate planning, requiring higher than optimum flow rates during delivery of the fluid to make up for the intermittent interruptions in flow so that the time-averaged flow rate to the patient will be optimal. Unfortunately, the necessity for higher than optimal flow rates interspersed with interruptions thereof can cause both harmful excessive concentrations of infused fluids at some times, and harmful insufficient concentrations at other times. The peristaltic type infusion pumps such as those shown in U.S. Pat. Nos. 3,73,930, 3,737,251 and 3,841,799, on the other hand, although providing substantially continuous flow, do not have the necessary accuracy of flow rate control provided by the syringe-type pumps and cannot therefore be used where a high degree of precision is required.

Another problem with prior infusion pump units is that their pumping and valving structures, even when provided in easily replaceable cassette form, lack the compactness and simplicity to provide a high degree of portability and versatility for both hospital and home use. Although some units, such as those shown in U.S. Pat. Nos. 3,456,648 and 3,994,294, employ simplified valving which utilize tube-deforming devices for selectively opening and closing fluid conduits, the means of packaging such simplified valving systems in a highly compact, replaceable cassette form have not been known.

Although highly accurate stepper motors have been used to control infusion pump flow rates, as exemplified by the aforementioned U.S. Pat. Nos. 3,736,930 and 3,985,133, the frequency control of pulses driving such motors does not provide adequate insurance that the commanded flow rate will actually occur, particularly under variable back pressure conditions. The same is true of pulsed, nonstepping motors utilized in pumps such as those shown in the aforementioned U.S. Pat. Nos. 3,858,581 and 4,367,435, where transient load conditions may likewise prevent the motor from moving in accordance with the drive pulses Moreover, the aforementioned pulsed electric motors do not have optimal energy efficiency characteristics which enable them to maximize the life of a battery power source, which would enhance their portability. Usually the drive pulses are of a constant duration which is longer than necessary to advance the motor the necessary amount against normal back pressures, thereby consuming excess power.

Finally, although a number of the prior infusion pump devices include occlusion detection systems, such as those shown for example in U.S. Pat. Nos. 3,731,679 and 3,985,133, such systems provide insufficient control over the likelihood that a partial occlusion, such as a partially obstructed or pinched fluid outlet, will disable the system. Accordingly, in some cases, disabling occlusions occur with excessive frequency, requiring excessive supervision and correction by an attendant.

SUMMARY OF THE PRESENT INVENTION

The present invention is directed to an infusion pump having mutually-compatible features which overcome all of the foregoing drawbacks of the prior art. The pump may be used for intravascular, body cavity, eternal and other similar infusions.

Substantially continuous flow is made compatible with highly accurate volumetric flow control by employing a dual chamber piston and cylinder assembly with associated valving which pumps fluid to the patient at a predetermined volumetric flow rate while simultaneously drawing fluid from the fluid source at the same flow rate. Thus no interruptions of the flow for refilling are necessary, and the discharge flow rate is thus the actual desired optimum flow rate rather than a higher than optimal flow rate. These objectives are achieved in a pump housed in a highly compact, inexpensive, disposable cassette despite the need for twice as many pumping chambers and twice as much input-output valving as is employed in prior syringe-type pumps. This is made possible by the utilization of pairs of deformably-closable input-output tubes within the cassette structure, each pair being connected to a respective pump chamber, with a simple tube closure structure movably mounted on the cassette for controlling the selective opening or closing of all of the tubes simultaneously.

Improved reliability with respect to maintaining the desired fluid flow rate under variable load conditions, and improved energy efficiency of the pumping motor to enhance the battery-powered portability of the pumping unit, are achieved in the present invention by a motor control system which initiates motor driving electrical pulses at an adjustably variable, predetermined time rate dependent upon the desired flow rate, but terminates each of such pulses not on the basis of time but rather on the basis of position attained by the motor in response to the pulse. This control system has the advantage of shortening the duration of each electrical pulse if light load conditions permit the motor quickly to attain a predetermined increment of advancement in response to a pulse, thereby saving energy. Alternatively, the system provides longer pulse durations if high load conditions, in the form of high back pressure, tend to retard the advancement of the motor in response to each pulse. Such variable, load-dependent pulse durations increase the likelihood that the pump will reliably deliver the required increment of fluid in response to each electrical pulse even under conditions of high loading.

Finally, the occlusion-detection system of the present invention, which monitors the average rate of movement of the pump-motor, is accompanied by a system for controllably varying the time-averaged electrical current driving the pump motor so as to controllably vary the maximum pressure of fluid pumped to the patient. This enables the operator to vary the degree to which the infusion pump is susceptible to being retarded by back pressure, enabling the use of different pumping pressures when appropriate to compensate for loading conditions which vary from patient to patient. Thus, for example, if a particular patient has a propensity for retarding the pump with excessive frequency, the operator has the ability to correct this problem by increasing the electrical current to raise the pump's output pressure.

The foregoing and other objectives, features and advantages of the present invention will be more readily understood upon consideration of the following detailed description of the invention, taken in conjunction with the accompanying drawings.

BRIEF DESCRIPTION OF THE DRAWINGS

FIG. 14 is a table showing the pump drive motor commutation sequence in reversible directions in accordance with FIG. 13.

FIG. 16 is an exemplary logic flow diagram according to which the microcomputer of the unit is programmed to control the pump drive motor.

DESCRIPTION OF THE PREFERRED EMBODIMENT

General Arrangement

Figure 1:
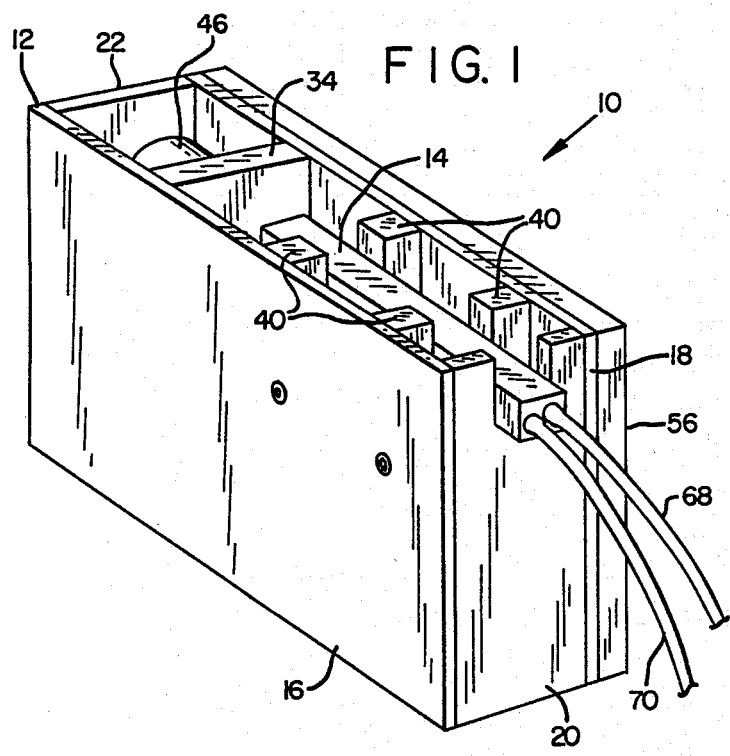
FIG. 1 is a perspective view of an exemplary embodiment of the infusion pump of the present invention, showing the base housing with a cassette inserted therein.
Figure 3:
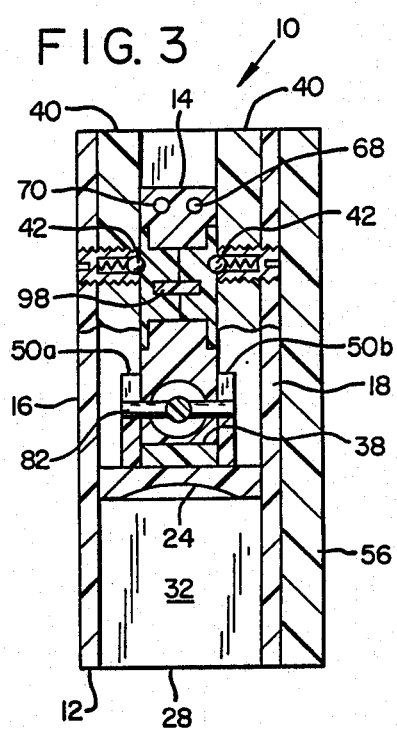
FIG. 3 is a cross-sectional view taken along line 3—3 of FIG. 2.
Figure 2:
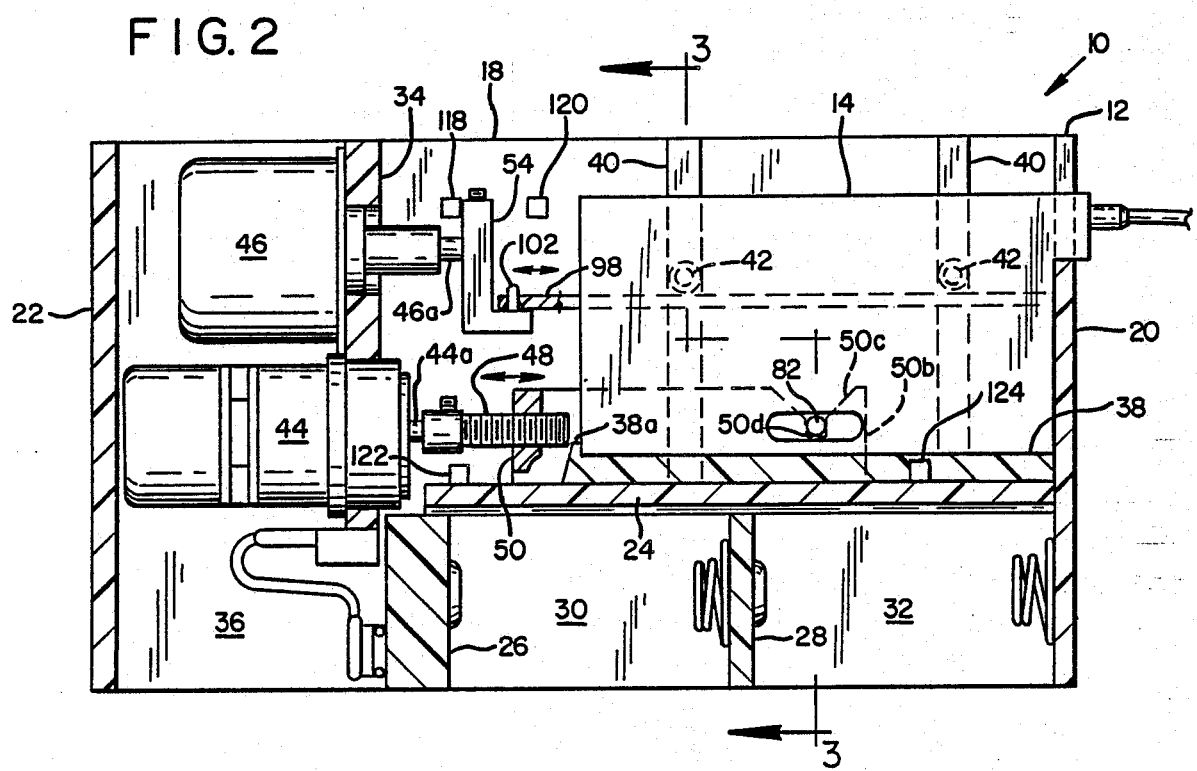
FIG. 2 is an enlarged, side-sectional view of the infusion pump of FIG. 1.
Figure 4:
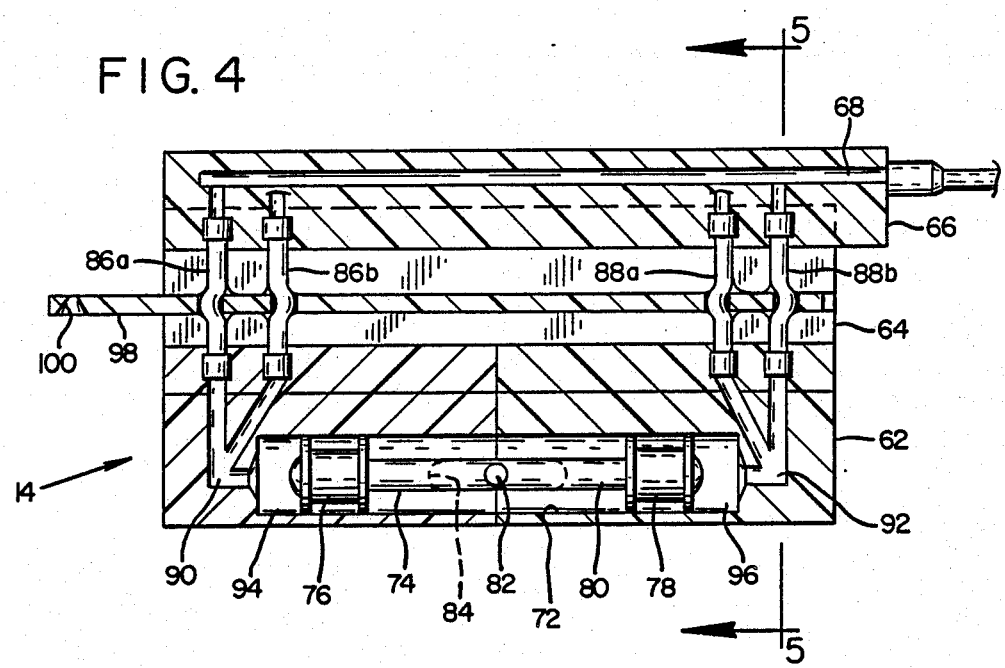
FIG. 4 is a side-sectional view of the cassette employed in the pump of FIG. 1.
Figure 5:
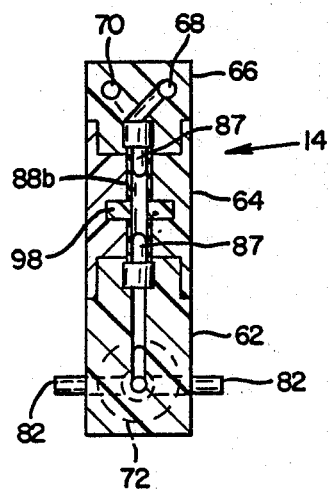
FIG. 5 is a cross-sectional view of the cassette taken along line 5—5 of FIG. 4.

The exemplary embodiment of the infusion pump of the present invention, indicated generally as 10 in FIG. 1, comprises a base member 12 which detachably houses an insertable cassette 14, both of which may be of impact-resistant plastic construction. The base 12 essentially consists of a rectangular housing having major sidewalls 16 and 18 and ends 20 and 22, with interior partitions 24, 26 and 28 defining battery compartments 30 and 32, partition 34 and end 22 defining a motor compartment 36, and ribs 38 and 40 together with end 20 defining a cavity into which the cassette 14 can be matingly inserted as shown in FIGS. 1-3. When so inserted, the major sides of the cassette are engaged by the ribs 40 and held in place by opposing pairs of detents 42 mounted in the ribs 40 which engage mating depressions in the sides of the cassette 14. The cassette is also restrained against movement along its length by the engagement of one of its ends with the end 20 of the base 12, and the engagement of its opposite end with a lug 38a protruding upwardly from the rib 38 upon which the cassette rests, as shown in FIG. 2.

Mounted on the partition 34 within the base 12 are a bidirectional pump-motor 44 and a bidirectional valve motor 46. The valve motor 46 is preferably a conventional linear actuator stepper motor having high reluctance or "cogging" force for holding position without energizing of the coils, so as to be capable of maintaining the valve assembly in the desired position without consuming battery power. The pump-motor 44, on the other hand, is a rotary motor preferably having little or no cogging torque. Both motors are powered by four rechargeable batteries which may be inserted in battery compartments 30 and 32 or, alternatively, by an external DC source.

Mounted on the drive shaft 44a of the pump-motor 40 is a screw member 48 threadably engaging the base of a U-shaped drive yoke 50 having a pair of spaced-apart legs 50a and 50b which straddle the sides of the cassette 14 when it is inserted in the base 12 as shown in FIGS. 2 and 3. Turning of the pump-motor 44 in one direction moves the yoke 50 away from the motor, while turning of the motor in the opposite direction retracts the yoke 50 toward the motor, the yoke being slidably supported for such reciprocative movement on the partition 24. The drive shaft 46a of the linear valve motor 46 is attached to an L-shaped valve controller 54, which reciprocates with respect to the motor 46 in a direction parallel to the direction of reciprocation of the yoke 50.

The base 12 also includes a control panel 56 attached to the side 18 of the base member. The control panel includes an LCD 58 for displaying total volume to be infused (cc), volumetric rate of infusion (cc/hr), volume currently infused, minimum rate of infusion to keep a vein open following total infusion (KVO), and output pressure setting. In addition, the LCD displays operating messages which assist the user in the input of new pump control settings, interpretation of error conditions, and determination of the unit's present operating mode. A key pad 60 permits the user to input desired settings by first pressing the "HALT/DATA" key, selecting the value to be modified by pressing one of the four "SET" keys, and then inputting the setting by depressing the appropriate numeric keys. The key pad 60 also provides a key for actuating a "PURGE" mode of the pump for the clearing of air from the system by running the pump at high speed while connected to the fluid source but not to the patient.

The electronic control circuitry for the unit, to be explained hereafter, is mounted within the control panel 56 and on the interior surface of the side wall 18 in the area bounded by the partitions 24 and 34 and the end wall 20.

The Cassette

As best seen in FIGS. 4–7, the replaceable, disposable cassette 14 has a generally rectangular body composed of a bottom portion 62 housing a double-acting piston pump assembly, a middle portion 64 housing a valve assembly, and an upper portion 66 housing a fluid inlet 68 for connection to a source of fluid (not shown) and a fluid outlet 70 for connection to a patient. The piston pump assembly comprises a cylindrical bore 72 formed in the bottom portion 62 and having a reciprocating piston assembly 74 therein consisting of two plungers 76 and 78 joined together by a rod 80 having a transverse pin 82 connected thereto and protruding transversely from the bore through respective slots such as 84 formed in both sides of the cassette. When the cassette is inserted downwardly into the base 12, the ends of the pin 82 are guided by respective V-shaped notches, such as 50c (FIG. 2) in each leg 50a, 50b of the yoke 50, into a closely mating rectangular notch 50d at the bottom of each V-shaped notch. This establishes a tight, detachable driving connection between the legs of the reciprocative yoke 50 and the piston rod 80 for driving the piston assembly 74.

Figure 6:
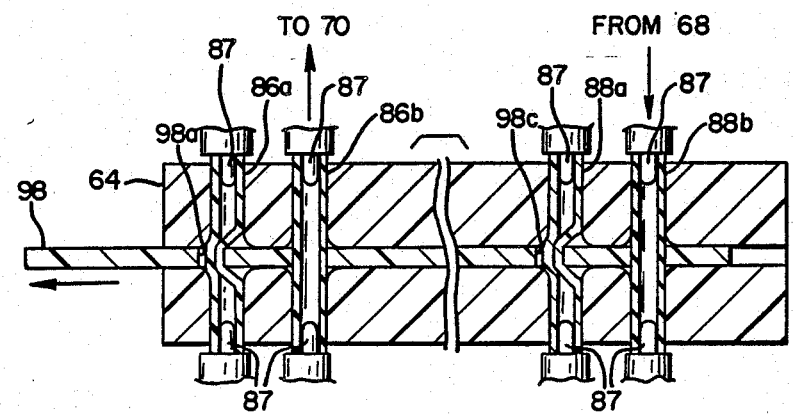
FIG. 6 is an enlarged, extended sectional view of the valve assembly of the cassette shown in its condition when the pump piston is moving in one direction.
Figure 7:
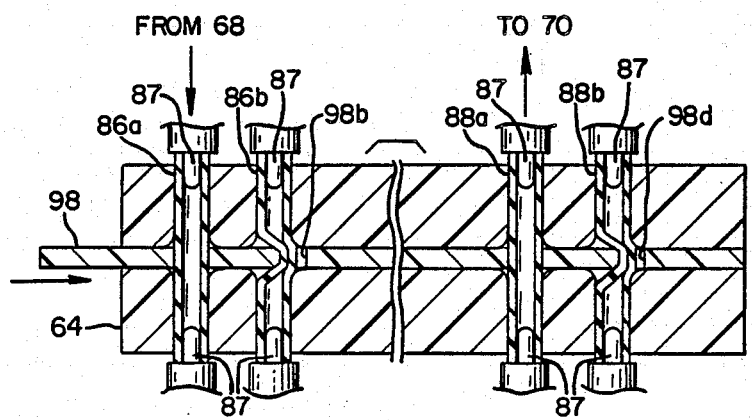
FIG. 7 is an enlarged, extended sectional view of the valve assembly similar to that of FIG. 6 showing the condition thereof when the pump piston is moving in the opposite direction.

The middle portion 64 of the cassette contains two pairs of normally open, deformably closable, resilient tubes 86a, 86b and 88a, 88b, respectively, each pair being interconnected through nipples 87 and conduits 90 and 92, respectively, with a respective fluid chamber 94 or 96 of the piston pump assembly. Tubes 86a and 88b are both connected to the fluid inlet 68, while tubes 86b and 88a are both connected to the fluid outlet 70. An elongate valve control member 98 is slidably mounted within the middle portion 64 of the cassette so as to move longitudinally with respect to the cassette in a direction parallel to the direction of movement of the piston assembly 74. As best seen in FIGS. 6 and 7, the valve control member 98 has four apertures 98a, 98b, 98c and 98d formed therein, each enclosing a respective one of the deformable tubes. The member 98 also has a portion protruding from one end of the cassette which includes an upwardly-tapered aperture 100 which, upon insertion of the cassette 14 into the base 12, engages an upwardly-protruding pin 102 (FIG. 2) on the L-shaped valve controller 54. The valve control member 98 has two alternative positions as shown in FIGS. 6 and 7, respectively. The position of FIG. 6, caused by the stepper motor 46 retracting the valve controller 54 in a direction toward the motor 46, deformably closes tubes 86a and 88a while permitting tubes 86b and 88b to remain open. Tube 88b exposes chamber 96 to fluid inlet 68 while tube 86b exposes chamber 94 to fluid outlet 70. This position of the valve control member 98 is used when motor 44 is retracting the yoke 50 toward itself, so that fluid is drawn from the fluid source into chamber 96 while it is pumped to the patient from chamber 94 simultaneously and at the same volumetric flow rate. Conversely, the other position of the valve control member 98 is that shown in FIG. 7, caused by motor 46 extending the valve controller 54. This position is used when motor 44 is extending the yoke 50 away from itself, since it opens tube 86a to draw fluid from the fluid source into chamber 94 while also opening tube 88a to pump fluid to the patient from chamber 96, closing the other tubes 86b and 88b. With the directions of the motors 46 and 44 properly synchronized such that valve control member 98 changes position when yoke 50 changes direction, fluid is pumped substantially continuously to the patient from the cassette while fluid is simultaneously drawn into the cassette from the fluid source substantially continuously and at the same volumetric flow rate.

General Description of Controls

Figure 8:
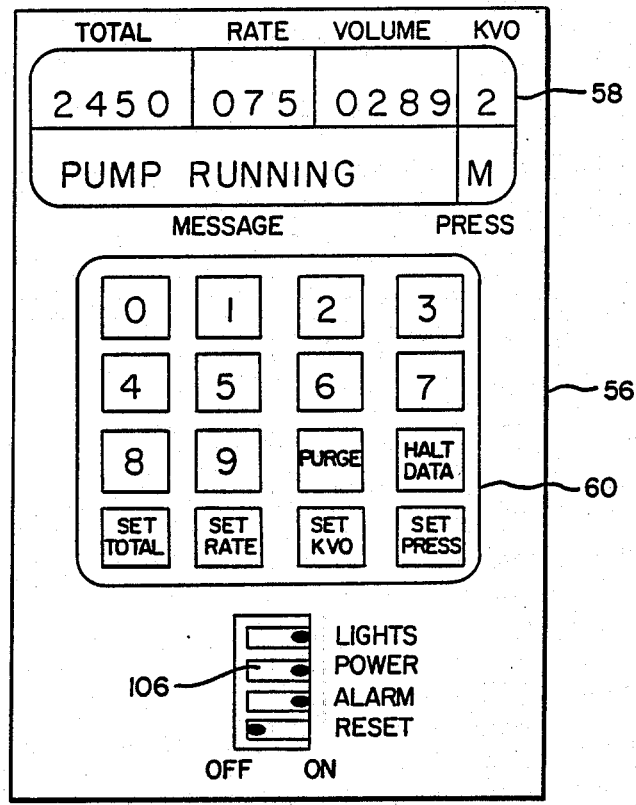
FIG. 8 is a front view of the control panel of the infusion pump of FIG. 1.
Figure 10:
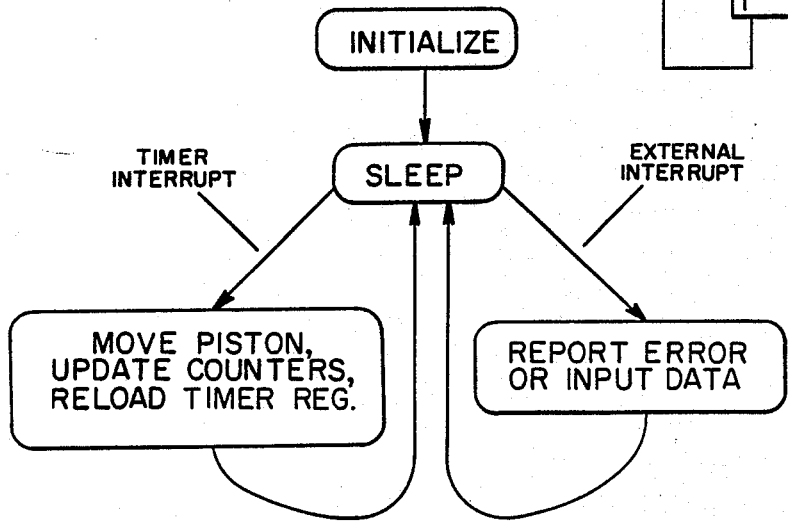
FIG. 10 is a diagram of the general functions of the microcomputer (MCU) of FIG. 9.

The control circuitry for the infusion pump is based upon a single chip microcomputer (MCU) such as the Hitachi Model HD6301V1 microcomputer. The program within the MCU is started with power-on switching by means of switch 106 (FIG. 8) and maintains and controls all pump functions while providing for user input and function display through the control panel 56. The MCU operates normally in the ultra low-power "sleep" mode (FIG. 10) but can be awakened by "interrupts" produced by one of several components of the control circuitry. First, under normal pump operating conditions, the volumetric rate of fluid infusion set by the user is translated by the MCU 104 into a time interval between the initiations of discrete pump motor drive pulses. This time interval is placed into a timer register, which keeps track of elapsed time regardless of the "sleep" condition of the MCU. When each time interval is completed, the MCU awakens, provides appropriate commands to the pump-motor and visual displays, and goes to sleep again. This cycle is repeated throughout the infusion. In addition, abnormal conditions can interrupt the sleeping state of the MCU. The operator could make changes to the pump control variables (rate, volume to infuse, etc.) by touching the "HALT/DATA" key, the appropriate "SET" key and the appropriate numeric keys, which interrupts the MCU. The input is processed, and the variables modified until the operator requests the pumping operation to resume by a second depression of the "HALT/DATA" key. Other conditions which interrupt the MCU are error states which may occur. These include such conditions as low battery power, external power interruption, air in line, etc.

Figure 9:
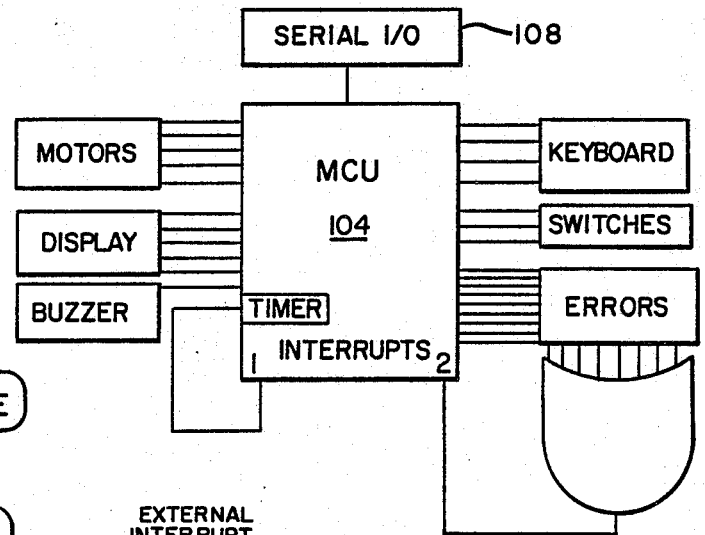
FIG. 9 is a block diagram of the major control circuit components of the pump of FIG. 1.

With reference to FIG. 9, the MCU has a serial I/O port 108 which provides for communication with a peripheral computer device or terminal if desired. This port could be used by a nurses' station to monitor the pump's performance, change settings, record pumping progress, etc., and can be used to "gang" several units infusing several fluids simultaneously.

Pump-Motor Control and Occlusion Sensing

Pump-motor 44 is preferably a noncogging, brushless, permanent magnet rotary motor of three-phase, four-pole design having three Hall effect sensors for monitoring position of the permanent magnet rotor and controlling the solid-state power drive switches (such as Darlington pairs) which commutate the three coil phases. Such motors are well-known, as evidenced for example by U.S. Pat. No. 4,130,769 which is incorporated herein by reference. However, in accordance with the special requirements of the present invention, the Hall effect sensors cooperate with the MCU 104 to control the power drive switches in a unique manner.

Figure 11:
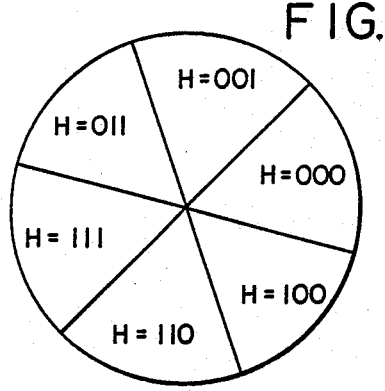
FIG. 11 is a schematic diagram showing an exemplary system by which the rotary position of the pump drive motor can be sensed using Hall effect sensors.
Figure 12:
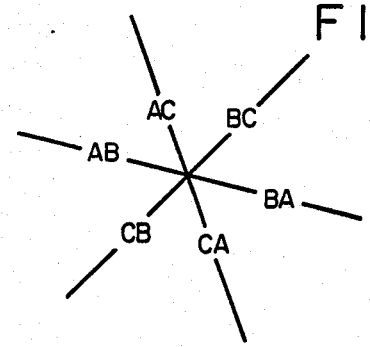
FIG. 12 is a schematic diagram showing an exemplary sequence by which the three phases of the pump drive motor may be commutated.
Figure 13:
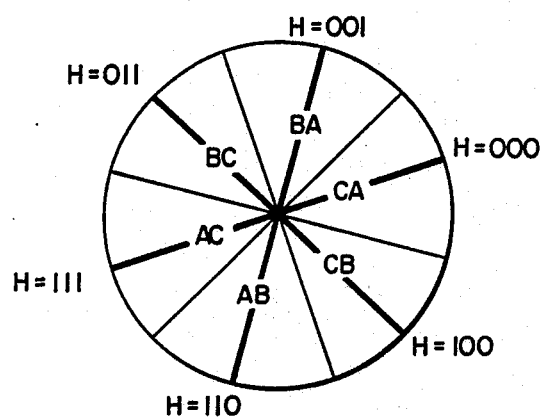
FIG. 13 is a schematic diagram showing the relationship between position-sensing and commutation of the pump drive motor in accordance with FIGS. 11 and 12.

FIG. 11 depicts six separate rotor position zones per revolution which the three Hall effect sensors are capable of detecting, together with the digital signals (for example "011") which the three Hall sensors produce when the rotor is anywhere within the corresponding zone. FIG. 12 shows the sequence of commutation of the three coil phases A, B, and C as the rotor rotates (e.g. "AB" indicates that phase A is connected to positive voltage and phase B is connected to ground while phase C is connected to neither). FIG. 13 shows how each of the six rotor position zones is correlated to the particular one of the commutations of FIG. 12 which is effective to move the rotor to the respective zone (e.g., if the rotor is at position "H=011", commutation "AC" will move the rotor to position "H=111"; conversely, if the rotor is at position "H=110", the same commutation "AC" will move the rotor to position "H=111" by reverse rotation). The table of FIG. 14 shows the entire commutation sequence for rotation in either a counter-clockwise or clockwise direction, representing a sequence of six motor-control bytes which are stored in the MCU 104 for outputting in sequence at the aforementioned time intervals predetermined by the volumetric flow rate selected by the user, each motor-control byte initiating a motor-driving electrical pulse.

Figure 15:
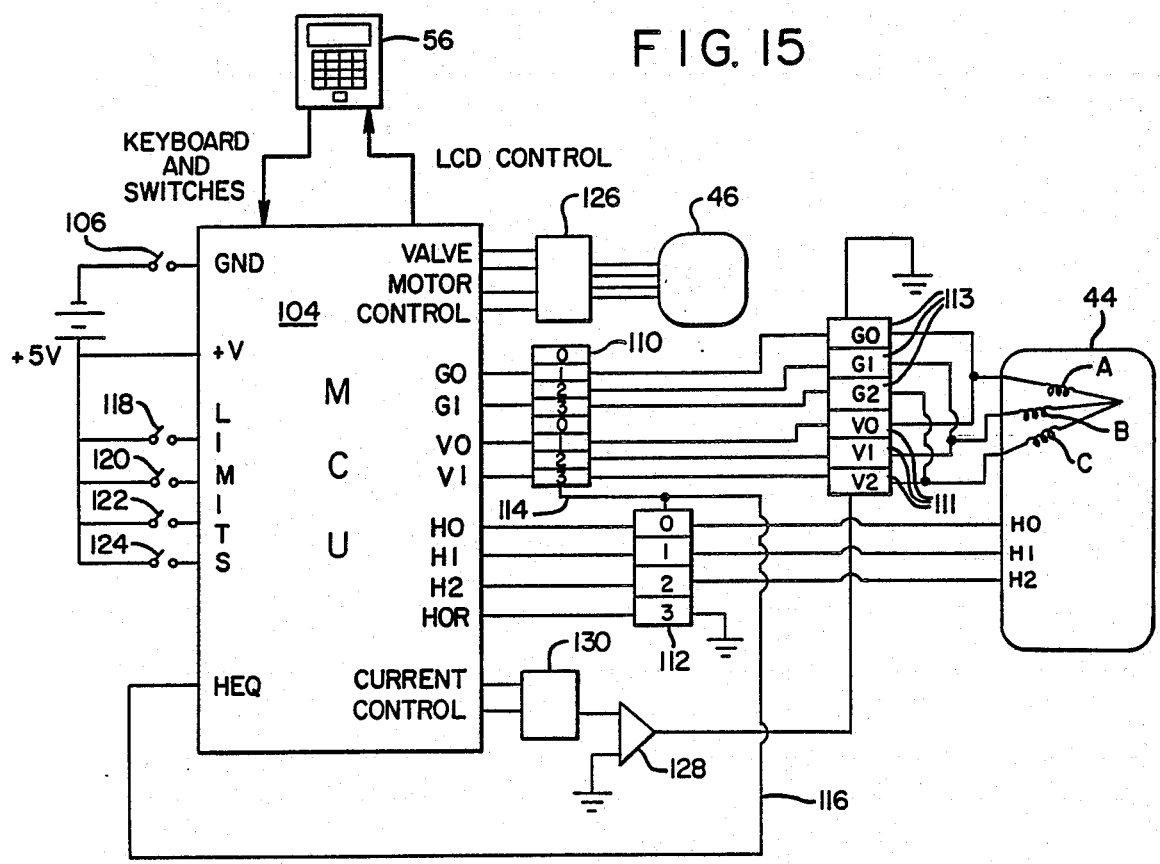
FIG. 15 is a schematic diagram of an exemplary pump drive motor and valve motor control circuit.

With reference to FIG. 15, each motor-driving pulse is initiated by the commutation information of the motor-control byte, designated by the bits V1, V0, G1, G0, respectively. These are fed to a dual two in——one out selector 110, which actuates one of the three switches 111 for connecting the appropriate one of the three phases A, B, C to positive voltage, and also actuates one of the three switches 113 for connecting the appropriate one of the other phases to ground. The motor-control byte thus written is the one which corresponds to the position zone immediately adjacent to the zone where the rotor is currently located, depending upon the desired direction of rotation. While the foregoing drive pulse-initiating portion of the motor-control byte is being provided to the selector 110, the position command portion of the same byte, designated in FIG. 15 by the bits H2, H1, and H0, is being supplied to a four-bit comparator 112. Simultaneously, the actual Hall effect position sensor readings from the motor 44 are also being supplied to the comparator 112. When the motor-control byte is first written and the drive pulse initiated, the commanded position and actual position will not be equal, and the comparator 112 will emit a low signal on line 114 which is necessary to enable the selector 110. However, as soon as the rotor has moved to the commanded position as a result of the drive pulse, the commanded position and actual position sensed by the comparator 112 will be equal, causing the signal in line 114 to go high, thus disabling the selector 110 and deactivating the power drive switches 111 and 113. Thus, although the motor drive pulses are initiated on a time interval basis, they are terminated on a position basis in response to the advancement of the rotor beyond a predetermined position (i.e., into a new position zone) after the initiation of the pulse.

Should the rotor, after initiation of a pulse, fail to attain the commanded position zone or if, having attained it, the rotor regresses from such zone, the output of the comparator 112 on line 114 will be low, enabling the selector 110 to drive the motor 44 toward the commanded position zone. Thus, the system automatically opposes any regression of the rotor, helping to ensure advancement of the motor especially under high load conditions. If the rotor cannot attain the commanded position zone, the MCU detects this condition by the absence of a high signal from the comparator 112 as sensed on line 116, in response to which the MCU, at the next pulse initiation time, writes the same motor-control byte previously written rather than the next one in the commutation sequence. The MCU counts the number of times this error condition occurs per cc of output fluid, and transmits an error signal in response to the error count exceeding a predetermined number.

The logic flow diagram by which the MCU 104 starts and controls the pump-motor 44 is shown in FIG. 16. To start the motor, the aforementioned error count is initialized to zero, and the present position of the motor is determined in the following manner. Starting at the top of the motor-control byte table of FIG. 14, the commutation information in the byte is masked off and the byte is then written. Since all commutation information is now zero, no power or ground can be connected to any phase. The Hall effect sensors feed actual rotor position to the comparator 112 where it is compared with the position command information in the motor-control byte. If they are unequal, the next motor-control byte in the table is written, and so forth until comparator 112 senses equality, at which time the signal in line 116 goes high establishing the starting point for the commutation sequence. Motor direction is determined by the location of the valve controller 54, as sensed by the closure of one of two limit switches 118 and 120 (FIGS. 2 and 15) or, alternatively, by Hall effect sensors (not shown) within the linear actuator valve motor 46. This information determines in which direction to initiate the commutation sequence. The next motor-control byte in the appropriate direction is written to initiate a motor-drive pulse and rotate the motor. When such drive pulse is terminated depends on whether the rotor has attained the commanded position zone as determined by the comparator 112 in accordance with the previous discussion.

At the end of an interval of time predetermined by the operator's selection of volumetric flow rate, the MCU reads the comparator's output signal on line 116 to determine whether or not the rotor has moved to the commanded position zone. If the signal on line 116 is low, indicating that the commanded position was not attained, the MCU increments the error count and determines whether the count has reached a predetermined maximum count. If not, the same motor-control byte previously written is rewritten at the end of the next time interval. But, if the maximum count has been reached, the MCU transmits an error signal which indicates that the average rate of movement of the motor 44 has been too slow. The error signal may disable the pump and/or actuate an alarm (not shown) mounted in the base 12, and/or write a message to a remote monitor which may be connected to the MCU.

Conversely, if a high signal on line 116 indicates that the commanded position zone has been attained, variables are updated to track progress of the infusion, and the next motor-control byte in the sequence is written. One of the updated variables is the cc-step count which signals the completion of each cc infused. After the infusion of each cc, the error count is cleared so that it can begin again. This feature makes the error count dependent upon the volume of fluid infused, providing a constant error tolerance per cc, as opposed to a variable error tolerance dependent upon motor speed.

When the yoke 50 reaches the end of its stroke in either direction, as indicated by its engagement with one of a pair of limit switches 122 and 124 (FIGS. 2 and 15), the MCU senses closure of the respective switch and actuates valve motor 46 through switch 126 to move the valve control member 98 rapidly to its opposite position for the return stroke of the piston assembly 74. The fluid is thus pumped continuously until the preset total volume to be pumped is reached, or until some error condition interrupts pumping.

Variably controllable output pressure of the pump is made possible by an amplifier 128 inserted in the main power line to the motor drive switches 111. The amplifier 128 variably regulates the time-averaged electrical current in response to a conventional digital-to-analog converter 130 which receives commands from the MCU 104 in response to the pressure setting entered by the user on the control panel 56, as previously described. The output torque of the pump-motor 44, and thus the output pressure of the fluid, is directly proportional to the time-averaged drive current as thus controlled, permitting adjustment of the fluid output pressure by the operator to compensate for excessive error counts due to external loading variables.

The bit indicated as "Hor" in FIG. 15 is a rotor position override, or "masking," bit capable of preventing the comparator 112 from outputting a high signal disabling the dual selector 110, regardless of rotor position. This bit can be used in high-speed applications, such as purging air from the system, where disabling of the selector 110 to terminate drive pulses is undesirable.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An infusion pump for administering fluid from a fluid source through an outlet to a patient at a controlled average volumetric flow rate comprising:
   (a) pump means for pumping fluid from said fluid source through said outlet at an average volumetric flow rate proportional to the average rate of movement of said pump means;
   (b) electric motor means for moving said pump means; and
   (c) control means for controlling the average rate at which said electric motor means moves said pump means, said control means comprising time-based means for repeatedly initiating motor-driving electric energy at a predetermined time rate, and position-based means for repeatedly terminating said energy in response to the advancement of said motor means beyond respective predetermined positions after respective initiations of said energy, said respective predetermined positions being separated by identical increments of movement of said motor means;
   (d) said electric motor means comprising a rotary brushless permanent magnet motor, having a rotor with permanent magnet poles and magnetic field sensor means for sensing the magnetic fields of said poles and thereby indicating the angular position of said rotor, said position-based means being responsive to the position of said rotor as indicated by said magnetic field sensor means.

2. The pump of claim 1 wherein said position-based means comprises means for enabling nonuniform durations of time between each successive initiation and termination of said energy.

3. An infusion pump for administering fluid from a fluid source through an outlet to a patient at a controlled average volumetric flow rate comprising:
   (a) pump means for pumping fluid from said fluid source through said outlet at an average volumetric flow rate proportional to the average rate of movement of said pump means;
   (b) electric motor means for moving said pump means;
   (c) control means for controlling the average rate at which said electric motor means moves said pump means, said control means comprising time-based means for repeatedly initiating motor-driving electric energy at a predetermined time rate, and position-based means for repeatedly terminating said energy in response to the advancement of said motor means beyond respective predetermined positions after respective initiations of said energy, said respective predetermined positions being separated by identical increments of movement of said motor means; and
   (d) comparator means for sensing whether or not said motor means has advanced beyond one of said increments of movement within a predetermined time period after an initiation of said energy.

4. The pump of claim 3, including means, responsive to said comparator means, for counting the number of times said motor means does not so advance, and transmitting an error signal in response to said number of times exceeding a predetermined number.

5. The pump of claim 4, including means for reinitiating said counting in response to the pumping of a predetermined volume of fluid by said pump.

6. The pump of claim 3 including means responsive to said comparator means for counting the number of times said motor means does so advance.

7. An infusion pump for administering fluid from a fluid source through an outlet to a patient, comprising:
   (a) fluid pump means connected to said fluid source and said outlet for pumping fluid from said fluid source through said outlet at a predetermined average volumetric flow rate;
   (b) electric motor means for driving said pump means;
   (c) sensor means for sensing the average rate of movement of said motor means;
   (d) means responsive to said sensor means for transmitting an error signal when the average rate of movement of said motor means, as sensed by said sensor means, is below a predetermined rate; and
   (e) means for controllably varying the time-averaged magnitude of electric current driving said motor means, so as to controllably vary the maximum pressure of said fluid pumped through said outlet, independently of the magnitude of said predetermined average volumetric flow rate so as to maintain said predetermined average volumetric flow rate in case of a partial occlusion tending to reduce said volumetric flow rate.

8. The pump of claim 7 wherein said sensor means includes means for sensing the average rate of movement of said motor means separately for separate predetermined volumes of fluid pumped by said pump means.

9. An infusion pump for administering fluid from a fluid source through an outlet to a patient at a controlled average volumetric flow rate comprising:
(a) pump means for pumping fluid from said fluid source through said outlet at an average volumetric flow rate proportional to the average rate of movement of said pump means;
(b) electric motor means for moving said pump means; and
(c) control means for controlling the average rate at which said electric motor means moves said pump means, said control means comprising time-based means for repeatedly initiating motor-driving electric energy at a predetermined time rate, position sensor means for sensing the position of said motor, and position-based means responsive to said position sensor means for repeatedly terminating said energy, said position-based means including means for terminating said energy concurrently with the advancement of said motor means beyond respective predetermined positions after the most recent initiation of said energy irrespective of the time elapsed since said most recent initiation, successive ones of said respective predetermined positions being separated by identical increments of movement of said motor means; and
(d) said means comprising reciprocative piston and cylinder means for pumping fluid through said outlet at said controlled average volumetric flow rate while simultaneously drawing fluid from said fluid source at said controlled average volumetric flow rate.

10. An infusion pump for administering fluid from a fluid source through an outlet to a patient, comprising:
(a) fluid pump means connected to said fluid source and said outlet for pumping fluid from said fluid source through said outlet at a predetermined average volumetric flow rate;
(b) electric motor means for driving said pump means;
(c) sensor means for sensing regressive movement of said motor means in a direction opposite to that in which said motor means drives said pump means; and
(d) control means responsive to said sensor means for initiating motor-driving electrical energy opposing said regressive movement in response to the sensing by said sensor means of said regressive movement.

* * * * *

UNITED STATES PATENT AND TRADEMARK OFFICE
CERTIFICATE OF CORRECTION

PATENT NO.   : 4,898,579
DATED        : February 6, 1990
INVENTOR(S)  : Leroy E. Groshong et al.

It is certified that error appears in the above-identified patent and that said Letters Patent is hereby corrected as shown below:

Abstract, line 16   Change "adjustable" to --adjustably--;

Col. 1,   line  5   Change "JUne" to --June--;

Col. 1,   line  5   Change "U.;S." to --U.S.--;

Col. 1,   line 40   Insert a period (.) after "times";

Col. 1,   line 42   Change "3,73,930" to --3,736,930--;

Col. 2,   line  3   Insert a period (.) after "pulses";

Col. 8,   line 27   Insert a period (.) after "sequence".

Signed and Sealed this

Twenty-first Day of May, 1991

*Attest:*

HARRY F. MANBECK, JR.

*Attesting Officer*         *Commissioner of Patents and Trademarks*